United States Patent [19]

Kell

[11] 4,412,916

[45] Nov. 1, 1983

[54] AIRLESS ARTIFICIAL KIDNEY ASSEMBLY

[75] Inventor: Michael J. Kell, Decatur, Ga.

[73] Assignee: Cordis Dow Corp., Miami, Fla.

[21] Appl. No.: 276,751

[22] Filed: Jun. 24, 1981

[51] Int. Cl.³ .............................................. B01D 31/00
[52] U.S. Cl. ..................................... 210/90; 210/188;
210/262; 210/296; 210/300; 210/309;
210/321.3; 210/335; 210/436; 210/456;
210/472; 55/159; 55/421
[58] Field of Search ...................... 210/87, 90, 94, 120,
210/188, 259, 260, 262, 295, 296, 300, 305–310,
321, 323, 335, 433, 436, 455, 456, 472, 927;
128/675, 748, DIG. 3, 214; 73/38, 714, 706,
715; 55/59, 318, 421

[56] References Cited

U.S. PATENT DOCUMENTS

| 3,447,570 | 6/1969 | Collins | 222/88 |
|---|---|---|---|
| 3,523,408 | 8/1970 | Rosenberg | 55/159 |
| 3,554,035 | 1/1971 | Buisson et al. | 73/726 |
| 3,713,341 | 1/1973 | Madsen et al. | 73/715 |
| 3,778,971 | 12/1973 | Granger et al. | 55/159 |
| 3,854,907 | 12/1974 | Rising | 210/436 X |
| 3,993,062 | 11/1976 | Jess | 55/159 |
| 4,004,587 | 1/1977 | Jess | 210/314 |
| 4,077,882 | 3/1978 | Gangemi | 210/90 |
| 4,184,489 | 1/1980 | Burd | 128/214 R |
| 4,231,871 | 11/1980 | Lipps et al. | 210/87 |

Primary Examiner—David R. Sadowski
Attorney, Agent, or Firm—Neal A. Waldrop; Jay C. Taylor

[57] ABSTRACT

The invention provides an artificial kidney extracorporeal circuit assembly including an artificial kidney having detachably attached multifunctional subassembly means for automatically venting gas bubbles from liquid flowing therethrough, for continuously sensing the liquid pressure of and for filtering said liquid, together with blood tubes for connecting a patient's artery to the kidney and the subassembly outlet port to a patient's vein.

The subassembly includes means associated with a hydrophobic gas bubble vent which prevent clogging, minimize blood clotting and insure against ambient gas entry through the vent.

14 Claims, 9 Drawing Figures

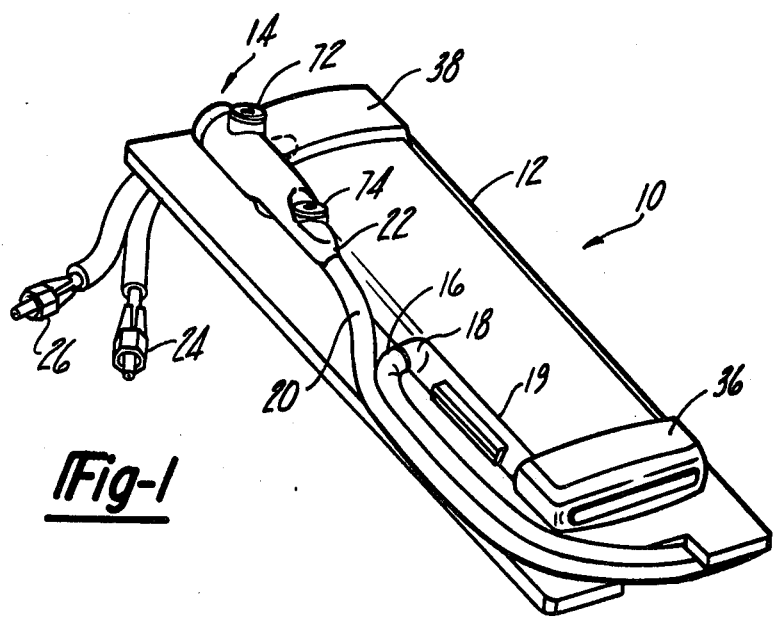
Fig-1
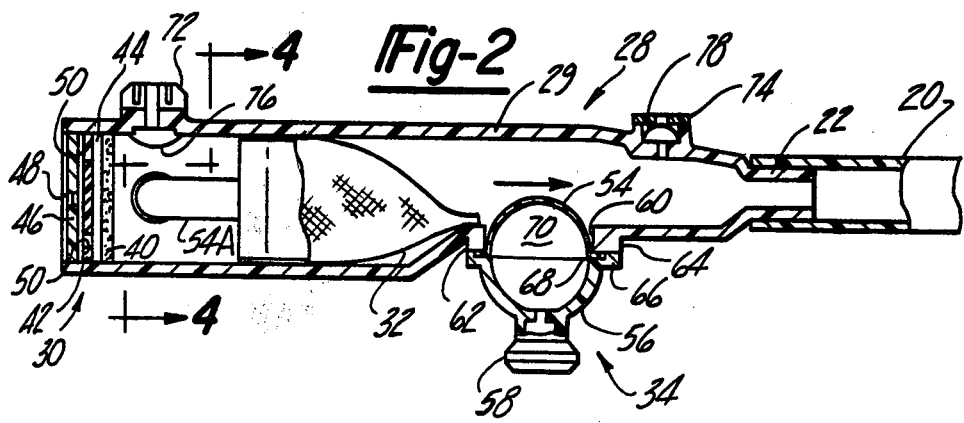
Fig-2
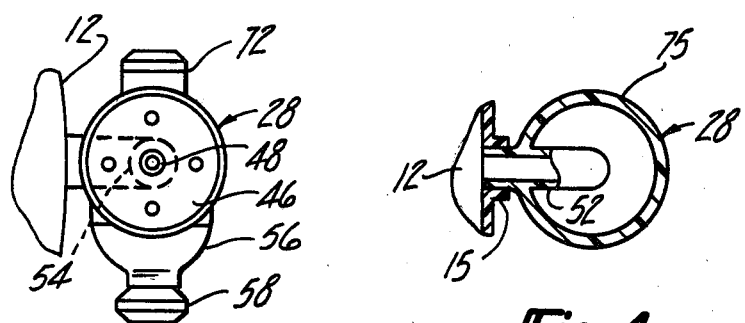
Fig-3
Fig-4

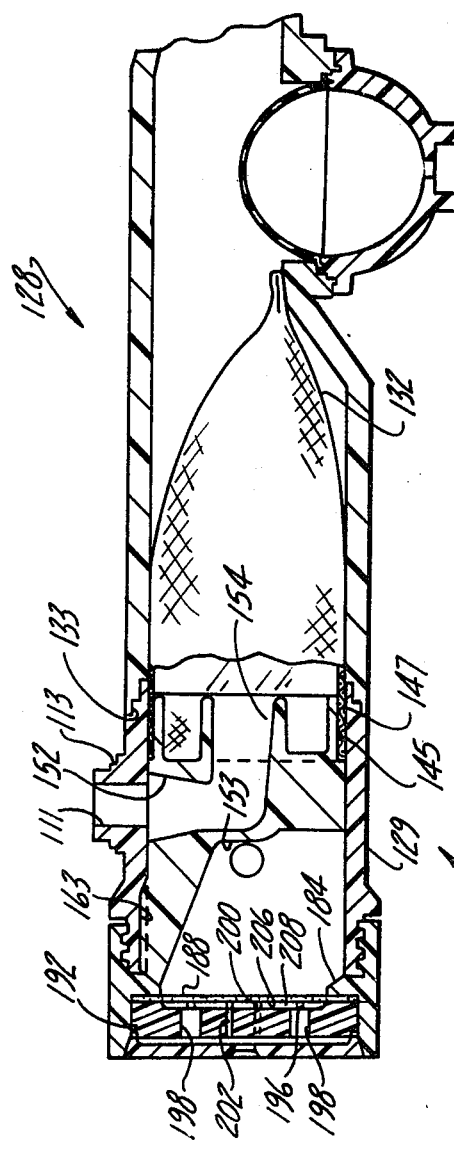
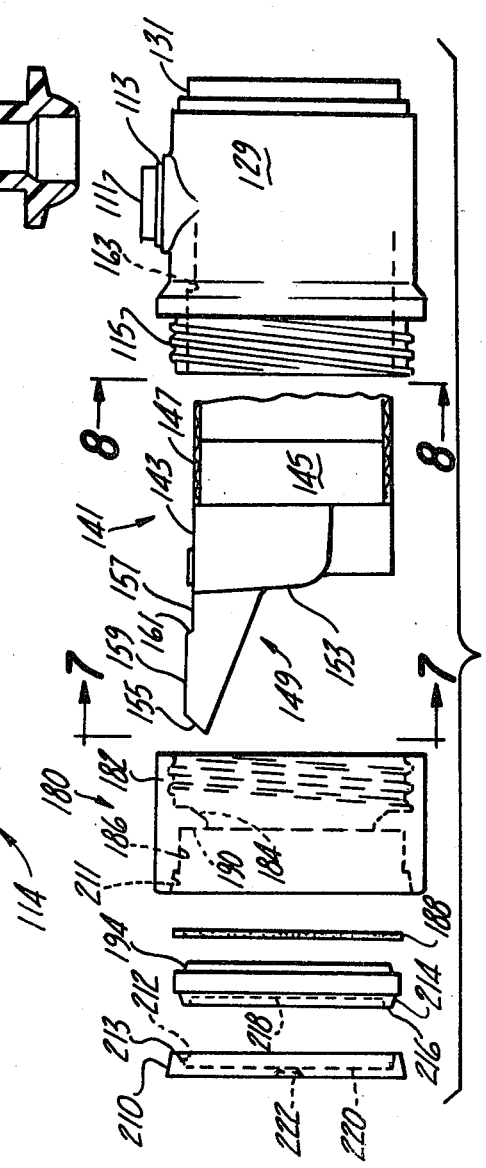

AIRLESS ARTIFICIAL KIDNEY ASSEMBLY

This invention is an improvement on the artificial kidney of U.S. Pat. No. 4,231,871 and more particularly on the kidney shown in FIG. 10 thereof.

BACKGROUND OF THE INVENTION

In hemodialysis treatments using an artificial kidney it is necessary, in the interest of patient safety, to monitor the positive pressure of the blood being returned to a patient's vein and to insure that the returning purified blood is free of particulate matter and gas bubbles. Heretofore, it has been conventional to perform the blood pressure measuring step by incorporating a venous drip chamber in the blood tube that is connected to the patient's vein.

Typically the venous drip chamber is secured to a stand or support adjacent the patient such that it remains upright during the treatment to insure the rise of gas bubbles to the top portion of the chamber. The bubble chamber serves the dual function of bubble removal and of providing a site for measuring the pressure of the blood in the return tube path to the patient's vein. The drip chamber is a closed receptacle and as pressure changes or separated bubbles add to the air space at the top of the chamber it is necessary, periodically, to inject a needle into the air space and suck out some of the gas to maintain a preset level in the chamber to avoid the possibility of air bubbles reaching the patient and causing a fatal embolism.

There are a number of undesirable aspects to the use of such venous drip chambers. First, repetitive needle penetrations increase the potential of creating a non-sterile circuit. Second, relatively constant observation of the blood level by the clinic attendant is required and personal withdrawal of excess gas requires time and effort during the normal four to six hour hemodialysis treatment. Third, there is a continuously existing blood-air interface within the drip chamber and the exposure of a patient's blood to air during the extended four or more hours during the hemodialysis treatment tends to degrade, contaminate, denature, or even clot the blood in the chamber. For this reason, a need for an airless artificial kidney system has been recognized since at least the early 1970's as hollow fiber artificial kidney use increased. FIG. 10 of U.S. Pat. No. 4,231,871 suggests the use of a microporous vent and blood pressure measuring means located in the venous line without showing a specific construction of either unit.

It was found that microporous vents having the form of a disc mounted at the top of a tubular shaped filter device, as shown in FIG. 10 of U.S. Pat. No. 4,231,871, had two operational problems. First, when using a hydrophobic material such as polytetrafluoethylene, having micro-sized openings in the range of about 1 to about 30 microns in the vent disc, clogging of the small openings with blood platelets occurred as the time of use extended and on occasion there was some foaming and some clotting of the blood adjacent the lower surface of the hydrophobic vent. Second, it was found that operating conditions which placed a negative pressure on the lower surface of the vent disc caused air to be drawn through the vent and into the blood chamber. The improved microporous vent containing subassembly of this invention overcomes both of these problems and provides an improved airless operating system, as will be explained in detail hereinafter.

Microporous vents per se and certain constructions using microporous vents to remove air, or entrained gases, from blood or other liquids prior to, or during, intravenous injection into a patient were known prior to this invention. Hydrophobic microporous membranes are shown in U.S. Pat. Nos. 3,778,971 and 3,993,062 and a combination of a hydrophilic and a hydrophobic separator is shown in U.S. Pat. Nos. 3,854,907, 4,004,587 and 3,523,408. These constructions employ tubular separator configurations, pouch-shaped devices as well as combinations of cylindrical separators with disc shaped separating membranes. The problem of ambient air entering into a gas separating filter is recognized in U.S. Pat. No. 4,190,426 and a variety of mechanical check valve constructions have been developed to overcome that problem and are discussed in a number of U.S. patents described in columns 1 and 2 of U.S. Pat. No. 4,190,426, which discussion is hereby incorporated herein.

The microporous vent construction of this invention employs a special housing configuration that includes only a hydrophobic separator and a novel, non-mechanical means to prevent the entry of ambient air into the filtering chamber.

In the past, measurement of blood pressure in the venous blood tube was accomplished by connecting a pressure transducer to the air space above the blood in the venous drip chamber since the pressure on the air in that space is the same as the blood pressure in the same chamber. As above stated, elimination of the blood-air interface is desirable and this invention employs pressure measuring means which does not require air, or gas of any composition, to interface with blood in the blood return path to the patient. Rather, blood pressure measuring means and the microporous vent are combined in a single tubular housing together with a blood filter that during hemodialysis operates completely filled with blood and free of air or other gas. The blood pressure measuring means employs a compressible diaphragm in a spherical or cylindrical receptacle mounted into the wall of the housing such that the diaphragm contacts the blood flowing through the housing as it returns to the patient. The blood pressure measuring receptacle contains air isolated from the blood in the housing by the compressible diaphragm. Movement of the diaphragm responsive to the pressure on the blood in contact with it in the housing expels air from the receptacle which is connected to a remotely located pressure indicator precalibrated to reflect blood pressure. Pressure detecting and measuring devices which include a deformable element having the shape of bellows, truncated cones, hemispheres or a diabolo are shown in U.S. Pat. No. 3,554,035. A frusto-conical, thin membrane disposed in a housing which transmits blood pressure variations through a pressure transmitting medium to a pressure transducer is shown in U.S. Pat. No. 4,077,882. Pressure transducers which employ flexible diaphragms have been used as gauges for gasoline or oil in U.S. Pat. No. 2,385,382, for sterile fluid measurements as shown in U.S. Pat. No. 3,818,765, and for blood as shown in U.S. Pat. No. 3,713,341. Pressure transmitting means responsive to pressure activated diaphragm elements include various fluids such as air, mercury, gasoline, etc., as shown in U.S. Pat. Nos. 2,369,707 and 3,349,623, or mechanical means as shown in U.S. Pat. No. 2,272,950. The above identified prior art represents the most pertinent art known to applicant relating to the separate microporous vent and diaphragm actuated pressure measuring elements which are satisfactory for use, in modified form, in the subassembly of this invention.

In addition to the automatic deaerating, blood pressure measuring, filtering subassembly of this invention, the overall airless artificial kidney assembly includes an artificial kidney and a blood tube for supplying blood from a patient's artery to the kidney and a blood tube for returning blood from the blood pressure measuring, air venting, filtering subassembly to the patient's vein. By virtue of combining the functions of automatic bubble separation and blood pressure measuring into a combination means that eliminates the need for a blood-air interface to enable pressure determination, it becomes possible to eliminate the conventional venous drip chamber as a part of the blood tubing set. Conventionally, blood tube sets have also included injection sites for heparin administration and blood sampling sites, which permit needle insertion through the blood tube wall. Constructions of such sites that assure safety to the nurse or technician using same are shown in shown U.S. Patents as Nos. 4,184,489, and 3,447,570. The direct, rigid attachment of the subassembly of this invention to the artificial kidney permits elimination of such separate blood tube site constructions by the incorporation of one or more of such sites into selected, accessible wall surface locations of the subassembly housing. The subassembly of this invention does include at least one such site. The elimination of the venous drip chamber and access sites from the blood tube set makes it feasible to flush and clean the blood tubes as well as the artificial kidney after a hemodialysis treatment to a degree of cleanliness that enables safe reuse of the blood tubes and the artificial kidney, whereas prior practice required discarding the entire blood tubing set. It remains desirable to discard the subassembly, or portions thereof, after a single use and to replace it, or the portions, with a substitute.

To the best knowledge of applicant, the assembly of this invention is the first artificial kidney assembly which has enabled the cleansing of a patient's blood in an extracorporeal circuit that is airless and free of a blood-air interface at any location in the extracorporeal circuit. It is also the first such assembly that has provided the option of safe reuse of the blood tubing as well as the artificial kidney.

SUMMARY OF THE INVENTION

The invention provides an improved extracorporeal hemodialysis treatment circuit which detoxifies blood in an airless artificial kidney assembly.

The assembly comprises an artificial kidney, a detachably attached multifunctional air venting, blood pressure measuring and filtering subassembly and blood tubes to connect the patient's artery to the kidney and the outlet port of the subassembly to a patient's vein. In the preferred embodiment the multifunctional subassembly combines and interconnects the vent, blood pressure measuring means and filter in a small, compact, common housing that may be easily disconnected from the kidney and blood tube and discarded after a single use to thereby enable safe reuse of the kidney and blood tubes by replacement of the discarded subassembly device. Alternately, the vent, blood diverter and the filter may be removed from the subassembly housing and replaced with substitute elements or cleaned and replaced prior to sterilization for reuse.

The multifunctional subassembly operates air-free and provides a microporous vent element in a modified configuration combining the filter and blood pressure measuring means, which minimizes blood denaturation and clotting and improves deaeration efficiency automatically during a hemodialysis treatment by means adopted to prevent clogging, or closing, of the micro-sized openings in a disc-shaped hydrophobic vent. The microporous vent configuration includes simple, non-mechanical means which prevent ambient gas ingress into the device through the vent in the event negative pressure develops on the lower surface of the vent disc during priming of the circuit prior to blood flow, or during the hemodialysis treatment.

BRIEF DESCRIPTION OF THE DRAWINGS

FIG. 1 is a perspective view of the artificial kidney assembly of this invention having a multifunctional subassembly attached to the upper end of the kidney.

FIG. 2 is an enlarged cross-sectional view of the multifunctional subassembly of FIG. 1 taken along the longitudinal center line thereof.

FIG. 3 is a top plan view of a broken away portion of the artificial kidney showing the attached subassembly of FIG. 2.

FIG. 4 is a cross-sectional view of the subassembly of FIG. 2 taken along the line 4—4 thereof.

FIG. 5 is a cross-sectional view of a modification of the subassembly of FIG. 1.

FIG. 6 is an exploded view of the parts of the modified subassembly of FIG. 5.

DETAILED DESCRIPTION OF THE PREFERRED EMBODIMENT

Figure 7:
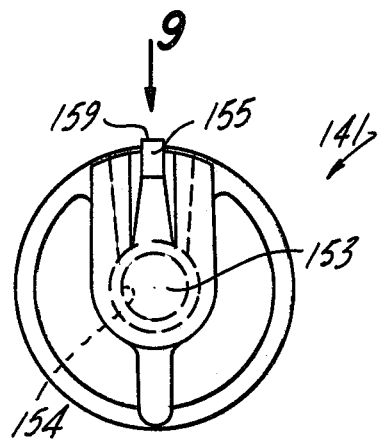
FIG. 7 is a view of the replaceable diverter element taken along line 7—7 of FIG. 6.

As shown in the drawings, the assembly of the invention, generally designated 10, comprises an artificial kidney 12, a multifunctional subassembly generally designated 14 and attached to the kidney outlet port 15 adjacent its upper end, a blood tube 16 attached to the inlet port 18 of kidney 12, and a blood tube 20 attached to the outlet port 22 of subassembly 14. Each of the opposite ends of blood tubes 16, 20 is provided with conventional attachment means 24, 26, respectively, for connection of the tubes to fistula means of conventional type.

Subassembly 14, as shown, comprises a generally cylindrical, elongated housing generally designated 28 which contains three integral, interconnected means which provide necessary functions to insure safe operation of assembly 10 in an extracorporeal circuit during hemodialysis treatment. The first means, generally designated 30, serves to automatically deaerate, or degasify, blood flowing into and from housing 28 by venting such bubbles to atmosphere. The second means is a filter 32. The third means, generally designated 34, is a blood pressure sensing device.

In normal use of assembly 10, blood from the patient's artery is fed through tube 16 into inlet port 18 of kidney 12, which as shown is a hollow fiber kidney of the type shown in U.S. Pat. No. 4,231,871. The blood then flows downwardly through integral blood channel 19 into the lower end header portion 36, then moves upwardly through the interiors of the thousands of semipermeable hollow fibers (not shown), then outwardly through upper header 38 into subassembly 14, and downwardly in the direction of the arrow shown in FIG. 2 for return to the patient's vein through blood tube 20.

Automatic deareation means 30 comprises a hydrophobic disc-shaped membrane 40 mounted so as to enclose the upper end of housing 28 at a location spaced upwardly from the point of entry of inlet tube 52 into housing 28, a cover 42 spaced a small distance above the upper surface of membrane 40 and secured to, or into, the wall of housing 28 so as to form a liquid-tight chamber 44 between the upper surface of membrane 40 and the lower surface of cover 42. An overlying gas-venting closure member 46 having a centrally located vent opening 48 is sealed into the upper end of housing 28. The lower surface of closure 46 is spaced slightly upwardly from the top surface of support 42. Chamber 44, when filled with water, or the like, through vent 48 and the plurality of apertures 50 in support 42, forms a thin layer of liquid, which overlies the upper surface of membrane 40 and sealingly separates the upper surface of membrane 40 from the ambient atmosphere. The thin layer of water permits gas bubbles migrating upwardly through the micro-sized pores in membrane 40 to pass through the water layer to atmosphere while concurrently preventing atmospheric gases from moving downwardly and through membrane 40 into the interior of housing 28. This simple inexpensive arrangement of parts to provide a liquid chamber 44 contiguous to the upper surface of membrane 40 insures against retrograde in-flow of atmospheric gases into housing 28 at any time the pressure on the lower surface of venting membrane 40 may become lower than atmospheric. Such conditions, although abnormal, may exist, for example during priming of the circuit prior to hemodialysis use as sterile saline is pumped through the arterial blood line and through the kidney, or such lowered pressure may occur during hemodialysis in the event of stopping, or malfunction, of the blood pump which normally maintains the desired blood pressure during hemodialysis treatment, i.e., a pressure in the range of about 35–250 mm. of mercury above normal atmospheric pressure.

Microporous vent 40 may be satisfactorily made from any hydrophobic membrane material having a structure that permits permeation of air, or gas, through the thin layer of the material and concurrently prevents the migration of blood or other aqueous liquid through the layer under the positive pressures that may be encountered during normal or abnormal conditions of use, that is, at pressures between about 10 and about 400 mm. of mercury above normal atmospheric pressure. Hydrophobic material such as the polytetrafluoroethylenes, polyfluoro-chloroethylenes, polyethylenes, polypropylenes and the like are satisfactory. Polytetrafluoroethylene is preferred and is commercially available with micro-pore sizes varying from 0.02 to 30 microns under the trademarks TEFLON or GORE-TEX from DuPont, Wilmington, Del., or W. L. Gore & Associates, Elkton, Md., U.S.A., respectively.

It was found that a polytetrafluoroethylene membrane having an average pore size of 0.2 micron possessed the best bubble venting to atmosphere characteristics but the pores of the membrane had an unacceptable tendency to clog with blood components, probably platelets or micro-clots, when blood entered the chamber of housing 28 closely adjacent the lower surface of vent 40 and continuously flowed past, or bathed, that lower surface. It was found, however, that such pore clogging could be eliminated or minimized by creating a stagnant layer of blood immediately adjacent the lower surface of vent 40. Deaeration means 30 provides a preferred construction which insures maintenance of the required thin, stagnant blood layers in contact with the lower surface of vent 40. Blood entering kidney outlet port 15 passes into housing 28 through blood flow directing, or baffling, means 52 which is a tube sealingly fitted into kidney port 15 and which directs incoming blood laterally into housing 28 to its axial center line and then bends downwardly in a 90° bend, as shown, into a tube portion 54A which extends along the longitudinal axis of housing 28 and directs blood flow into filter 32 in the direction of the arrow, FIG. 2. The 90° angle of deflection of tube 52 has been found to maximize the depth of the stagnant blood layer adjacent vent 40 and the lack of pore clogging with blood during hemodialysis usage, but it is to be understood that other angles less than 90° that direct blood flow from parallel to the lower surface of vent 40 and downwardly into housing 28 are suitable for use. Moreover, the blood tube 52 may be satisfactorily replaced with any baffling member, or other means, which projects into the incoming blood path and deflects blood flow away from vent 40 such that the required stagnant blood layer immediately adjacent the lower surface of vent 40 is preserved.

Filter 32 is sealed to the inner wall 29 of housing 28 by any suitable means, such as heat sealing, ultrasonic welding, press fit, or the like, to insure that all of the blood which enters housing 28 will pass through the filter before it reaches outlet port 22. Filter 32 may be fabricated from any blood compatible filtering material having a pore size which permits easy passage of blood therethrough and separates any debris or solids that may have entered the blood in the prior traverse through the inlet blood line 24 or kidney 12. A number of commercially available and heretofore used filters that are well known to those skilled in this art may be satisfactorily employed. As shown, the preferred filter 32 tapers gradually inwardly from its upper end toward its sealed lower end, but this shape is only desirable rather than necessary.

Blood pressure sensing, or measuring, device 34 is a gas tight receptacle formed of a generally hemispherical-shaped compressible, or flexible, diaphragm, or dome, member 54, which projects from the wall of housing 28 inwardly, and a rigid, generally hemispherical-shaped dome 56, which projects outwardly from housing 28, and is provided with an integrally attached gas outlet port 58. As shown, rigid dome 56 is attached to an opening 60 in the wall 29 of housing 28 defined by outwardly projecting bosses 62, 64 by heat sealing or ultrasonic welding of the opposed peripheral ledge 66 which locks the peripheral edge 68 of diaphragm 54 between bosses 62, 64 and ledge 66 and thus forms a gas tight cavity 70 in device 34. Outlet port 58 is adapted for connection to means for transmitting gas to a remotely located pressure gauge or pressure measuring means of conventional type such as a pressure transducer or the like, not shown. Pressure sensing means 34 functions to reflect small changes in pressure of the blood flowing in housing 28 and the consequent deflection of the flexible convex dome 54 into cavity 70 as pressure increases, and vice versa. The gas that is thus displaced is transmitted to a previously calibrated pressure transducer, not shown, to provide a continuous pressure indication on a conventional indicator, or the transmitted gas may be used to activate an alarm or pressure control means to maintain the preset safe pressure level of normal operation.

Diaphragm 54 may be made from any blood compatible flexible material such as silicone rubber. The preferred shape for positive pressure measurement is the convex hemispherical shape as shown. It is to be understood that a blood pressure sensing device similar to device 34 may be used in the arterial feed line between the patient's arterial fistula and a blood pump, if desired. In that event, blood sensing device 34 would be modified to operate at negative pressures, that is pressures less than normal patient blood pressure of 50–75 mm. of mercury. The only modification required is to employ a generally similar diaphragm of concave configuration instead of the inwardly projecting portion 54. The concave diaphragm will function similarly by contact with the blood in housing 28. In either the concave or convex configuration, diaphragm 54 is preferably tapered from its peripheral edge toward its crown to counteract hysteresis losses in its flexures and attain the highest degree of response to extremely small changes in pressure. For example, for a two centimeter diameter diaphragm 54, diaphragm thickness at the periphery of 0.02 inch is gradually thinned to the apex, or hemispherical central portion, to a thickness in the range of about 0.005 to 0.008 inch.

Housing 28 is provided with injection site 72 and sample site 74. Each is provided with a penetrable resilient seal, or closure, member 76, 78, respectively, for permitting conventional needle entry to the blood in housing 28 for such typical purposes as injecting medicants into the blood through site 72 and sampling the blood through site 74 or vice versa. As shown, sites 72, 74 are located on the exposed upper surface of housing 28 when it is attached to kidney 12 to insure easy, convenient access as desired during ordinary hemodialysis treatment usage.

Figure 8:
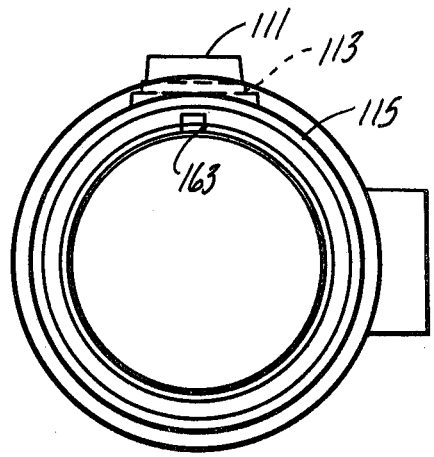
FIG. 8 is a view of the lower end portion of the housing of the subassembly of FIG. 5 taken along the line 8—8 of FIG. 6.
Figure 9:
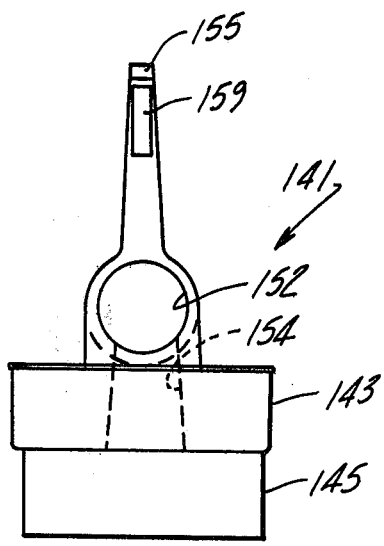
FIG. 9 is a side view of the replaceable diverter of the modified subassembly of FIG. 5.

In the modified form of the subassembly 14 which is shown in FIGS. 5–9, a design is provided which enables replacement of only a portion of the subassembly after each use. The subassembly is altered majorly in the upper end portion such that the blood diverter and microporous vent can be removed by disassembly and replaced; the filter may also be removed and replaced, if desired. The modified subassembly also makes possible the removal of the blood diverter, the vent and the filter element for cleaning outside the housing. The cleaned elements prior to sterilization for reuse.

Referring particularly to FIGS. 5 and 6, the modified subassembly 114 includes an upper wall portion 129 of the housing 128 that is provided on its lower end with a double ledge portion 131 for attachment or joining to a mating ledge portion 133 of wall 129 by any suitable means such as adhesives, ultrasonic welding or the like. Wall portion 129 includes a blood inlet port 111 having stepped ledges 113 for attachment to mating stepped surfaces in the kidney port, not shown, and terminates at its upper end in an externally threaded connecting portion 115.

The replaceable blood diverter generally designated 141 is a one-piece, cylindrically shaped member having a blood inlet tubular portion 152 and a downwardly extending, axially located diverter portion 154. Blood diverter 141 has an outside diameter portion 143 adapted to snugly interfit with the inside diametral surfaces of wall 129 and an undercut smaller diameter portion 145 (FIG. 9) which is adapted to abut and be surrounded by the upper end portion 147 of filter 132. Diverter 141 has an upwardly extending, generally triangular shaped locator arm member 149 which tapers from the upper surface 153 of inlet tube 152 outwardly and upwardly to a reversely tapered upper end ledge 155. The peripheral portion 157 of arm 149 has the same outside diameter as the lower portion 143 and is provided adjacent its upper end with a longitudinally extending locator key 159 having a lower end tapered surface 161 which is adapted to interfit with slot 163 in the upper end of wall 129 as an assist during assembly.

A removable cap generally designated 180 is provided with an internally threaded portion 182 adapted to mate with the external threads 115 and to apply axial sealing pressure to force blood diverter 141 into the position shown in FIG. 5 as the circumferential tapered ledge 184 bears against the correspondingly tapered ledge 155 during assembly. Cap 180 is an open ended cylindrical shell having a cavity 186 for receiving and supporting microporous vent membrane 188 on the upper end surface 190 of ledge 184. Vent membrane 188 is secured in place by cover disc 192 having circumferential projection 194. The lower surface 196 of disc 192 is also provided with additional supports for membrane 188 in its central region to prevent collapse in the event of large pressure gradients across the membrane. These additional supports are circular and consist of two projecting beads. Bead 196 has a diameter which bisects the central portion of four equally arcuately spaced apertures 198 which extend through disc 192 and provide the escape route for part of the gases that exit to atmosphere. The second bead 200 has a smaller diameter than bead 196 and supports membrane 188 immediately adjacent to three equally arcuately spaced apertures 202 that similarly extend through disc 192.

The lower surface 204 of disc 192 and the upper surface 206 of membrane 188 define a liquid tight cavity 208 which during use is filled with water for the identical purpose described above in connection with chamber 44 in the embodiment of FIG. 2. Disc 192 is maintained in pressure sealing contact with the portion of membrane 188 which overlies support surface 190 of cap 180 by upper closure 210. Tapered portion 212 of circumferential bead 213 of closure 210 bears against the upper tapered surface 214 of bead 216 which projects upwardly from the upper surface 218 in disc 192 when closure 210 is inserted into opening 211 of cap 180 and sealed thereto by any suitable means. The upper end of apertures 198 and 202 open into planar surface 218 which is spaced downwardly from the lower surface 220 in closure 210 and the space between surfaces 218 and 220 provides a path for gases from apertures 198, 202 to move toward centrally located exit opening 222 in closure 210.

It will be apparent to one skilled in this art that the modified construction of subassembly 114 enables disassembly by unscrewing cap 180 from the threaded portion 115 of wall portion 129. With the upper end of housing 128 thus opened, blood diverter 141 with attached filter 132 is easily removed for discard and replacement of the cap, diverter and filter, or any one of them as elected. Filter 132 is also easily disassembled from diverter 141 and after cleaning each may be replaced in housing 128 for reuse after appropriate sterilization with, for example, a conventional formaldehyde solution.

I claim:

1. An airless artificial kidney assembly comprising
   (1) an artificial kidney having inlet and outlet ports,
   (2) a liquid-tight subassembly having a filter, microporous vent means for venting to atmosphere gas bubbles separated from liquid in said subassembly and preventing gas entry through said vent means into said subassembly, pressure measuring means for continuously monitoring the pressure of liquid in said subassembly, a housing for blood having an upper region and an outlet connector communicating with said housing for discharging blood therefrom,
   (3) a first tube secured at one end to said kidney inlet port and terminating at its opposite end in a connector for connecting said first tube with a patient,
   (4) a second tube secured at one end to said outlet connector of said subassembly and terminating at its opposite end in a connector for connecting said second tube with a patient,
   (5) said kidney outlet port opening into said housing for discharging blood thereinto,
   said filter being arranged for filtering blood flowing from said kidney outlet port to said outlet connector, said vent means comprising an upwardly opening microporous hydrophobic vent in communication with said upper region of said housing for receiving and discharging air bubbles therefrom, and means containing an aqueous solution overlying said vent for preventing downward flow of air through said vent into said housing.

2. An airless artificial kidney assembly as claimed in claim 1, said vent means comprising a horizontal disc having interior and exterior surfaces, said means containing an aqueous solution comprising a cover secured to said housing and spaced from and overlying the exterior surface of said vent to provide a container for said aqueous solution, said cover being apertured for passage of water therethrough.

3. An airless artificial kidney assembly as claimed in claim 2, wherein a second cover is secured to said housing and spaced from and overlying the first named cover, said second cover having an aperture for passage of water to enable filling of said container from the exterior of said assembly.

4. An airless artificial kidney assembly as claimed in claim 1 wherein said kidney is a hollow fiber artificial kidney, said subassembly, filter, vent and pressure measuring means are contained in a single housing detachable from said kidney and said second tube and wherein said vent is located adjacent the upper end of said housing, said pressure measuring means is located adjacent the lower end of said housing and said filter is located between said vent and said pressure measuring means.

5. A multi-functional, liquid-tight subassembly for attachment to an artificial kidney for filtering flowing liquid, automatically separating gas bubbles from liquid therein, and continuously monitoring pressure of liquid therein which comprises
   (1) a hollow elongated housing having upper and lower ends,
   (2) liquid inlet means adjacent one end of said housing,
   (3) liquid outlet means adjacent the opposite end of said housing,
   (4) a microporous vent sealingly enclosing the upper end of said housing at a location above said inlet means, said vent having interior and exterior surfaces,
   (5) means for effecting a stagnant pool of fluid immediately adjacent the interior surface of said vent comprising diverting means within said housing adjacent to said liquid inlet means for diverting the direction of flow of liquid entering said housing through said liquid inlet means initially directly away from said interior surface of said microporous vent for preventing said flow from sweeping across said interior surface of said microporous vent,
   (6) a filter in said housing below said inlet means for filtering fluid flowing in said housing from said inlet means to said outlet means,
   (7) pressure sensing means located below said filter in a wall of said housing for continuously sensing pressure changes in the pressure of liquid flowing through said subassembly.

6. A subassembly as claimed in claim 5, wherein said subassembly comprises said filter sealingly attached to the inner wall of said housing at a location below said inlet means to receive liquid diverted by said diverting means.

7. A subassembly as claimed in claim 5 wherein said microporous vent is overlaid with cover means spaced above said vent, said cover means provided with at least one aperture for venting gas through said microporous vent to atmosphere.

8. A subassembly as claimed in claim 5 wherein said microporous vent is overlaid with cover means spaced above said vent, said cover means provided with at least one aperture for venting gas through said microporous vent to atmosphere, and wherein said vent is hydrophobic and overlaid with water in the space between the upper surface of said vent and the lower surface of said cover.

9. A subassembly as claimed in claim 5 wherein said liquid pressure measuring means comprises a compressible concave diaphragm extending into the cavity within said housing and forming the inner wall portion of gas-tight receptacle having means for attaching a tubular connector on the outer wall portion of said receptacle to pressure indicating means located remotely from said liquid pressure measuring means.

10. A subassembly as claimed in claim 5 wherein said housing is provided with at least one injection site located in the wall of said housing which faces outwardly when said subassembly is secured to the outlet part of an artificial kidney.

11. An airless artificial kidney assembly comprising
    (1) an artificial kidney having inlet and outlet ports,
    (2) a liquid-tight subassembly having a filter, microporous vent means for venting to atmosphere gas bubbles separated from liquid in said subassembly, pressure measuring means for continuously monitoring the pressure of liquid in said subassembly, a housing for blood having an upper region, and an outlet connector communicating with said housing for discharging blood therefrom,
    (3) a first tube secured at one end to said kidney inlet port and terminating at its opposite end in a connector for connecting said first tube with a patient,
    (4) a second tube secured at one end to said outlet connector of said subassembly and terminating at its opposite end in a connector for connecting said second tube with a patient, said kidney outlet port opening into said housing for discharging blood thereinto, (5) means for providing a stagnant pool of blood in said upper region of said housing, (6) said vent means being in communication with said stagnant pool in said upper region for receiving and discharging air bubbles therefrom, said means for providing said stagnant pool comprising baffle means within said housing adjacent to said inlet means for diverting the direction of flow of liquid entering said housing through said inlet means initially directly away from said vent means for preventing said flow from sweeping across said vent means, and said filter being arranged for filtering blood flowing in said housing from said kidney outlet port to said outlet connector.

12. An airless artificial kidney assembly as claimed in claim 11, said vent means comprising a microporous hydrophobic vent in communication with said stagnant pool and opening upwardly at the top of said upper region of said housing, and means for providing an aqueous layer above said vent for preventing gas entry through said vent into said housing.

13. An airless artificial kidney assembly as claimed in claim 12, said vent comprising a horizontal disc having an interior surface in communication with said stagnant pool and having an exterior surface, said means for providing said aqueous layer comprising a cover secured to said housing and spaced from and overlying the exterior surface of said vent to provide a container for said aqueous solution, said cover being apertured for passage of water therethrough.

14. An airless artificial kidney assembly as claimed in claim 13, a second cover secured to said housing and spaced from and overlying the first named cover, said second cover having an aperture for passage of water to enable filling of said container from the exterior of said assembly.

* * * * *